(12) United States Patent
Steele et al.

(10) Patent No.: US 8,491,888 B2
(45) Date of Patent: Jul. 23, 2013

(54) HIGHLY ABSORBABLE COENZYME Q10 COMPOSITION AND METHOD OF PRODUCING SAME

(75) Inventors: Donald R. Steele, Westlake Village, CA (US); William V. Judy, Bradenton, FL (US)

(73) Assignee: Softgel Formulators, Inc., Westlake Village, CA (US)

( * ) Notice: Subject to any disclaimer, the term of this patent is extended or adjusted under 35 U.S.C. 154(b) by 1544 days.

(21) Appl. No.: 11/744,439

(22) Filed: May 4, 2007

(65) Prior Publication Data

US 2007/0259034 A1 Nov. 8, 2007

Related U.S. Application Data

(60) Provisional application No. 60/797,877, filed on May 5, 2006.

(51) Int. Cl.
*A61K 38/43* (2006.01)
(52) U.S. Cl.
USPC ........................................................ 424/94.1
(58) Field of Classification Search
USPC ............................................... 424/93.1, 94.1
See application file for complete search history.

(56) References Cited

U.S. PATENT DOCUMENTS

| | | | |
|---|---|---|---|
| 4,325,942 A * | 4/1982 | Taki et al. | 424/94.1 |
| 6,197,349 B1 * | 3/2001 | Westesen et al. | 424/501 |
| 6,369,042 B1 * | 4/2002 | Oberthur et al. | 514/54 |
| 6,417,233 B1 * | 7/2002 | Sears et al. | 514/549 |
| 6,616,942 B1 * | 9/2003 | Udel | 424/451 |
| 6,623,734 B2 | 9/2003 | Udell et al. | |
| 6,955,820 B1 | 10/2005 | Udell | |
| 2002/0147356 A1 * | 10/2002 | Bonsignore et al. | 554/121 |
| 2003/0165438 A1 * | 9/2003 | Behnam | 424/49 |

OTHER PUBLICATIONS

Hawley's Condensed Chemical Dictionary (15th Edition), Definition "flaxseed oil" John Wiley & Sons Copyright / Pub. Date: @ 2007 p. 569 Author/Editor: By: Lewis, Richard J., Sr.*
"Saturated" Merriam Webster Online, http://www.merriam-webster.com/dictionary/saturated , 1 page accessed Nov. 30, 2010.*
"Oil" Merriam Webster Online, http://www.merriam-webster.com/dictionary/oil , 2 pages accessed Nov. 29, 2010.*
"Oil" WordNet Search 3.0, 1 page, accessed Nov. 29, 2010, http://wordnetweb.princeton.edu/perl/webwn?c=1&sub=C...o2=&o0=1&07=&o5=&01=&o6=&o4=&o3=&i=-1&h=000000&s=oil11/29/2010 4:16:45 PM.*
"Bees Wax" LipidBank, 9 pages, acessed Nov. 29, 2010, http://lipidbank.jp/cgi-bin/detail.cgi?id=WWA2101.*
D'Alonzo et al. "Glyceride Composition of Processed Fats and Oils as Determined by Glass Capillary Gas Chromatography" JAOCS, vol. 59, No. 7 (Jul. 1982) pp. 292-295.*
Biology Online.org, Definition "Lipid" 1 page accessed Dec. 20, 2011 at http://www.biology-online.org/bodict/index.php?title=Lipid&printable=yes.*

* cited by examiner

*Primary Examiner* — Jon P Weber
*Assistant Examiner* — Thane Underdahl
(74) *Attorney, Agent, or Firm* — Amin Talati, LLC; Janine A. Moderson; George M. Carrera, Jr.

(57) ABSTRACT

The present invention provides an essentially crystal-free, highly bioavailable and absorbable coenzyme Q10 (CoQ10) composition including CoQ10, a solvent, and a carrier oil for supplementing nutrition and for use as an antioxidant. The present invention further provides method of increasing the absorption and bioavailability levels of coenzyme Q10 in the blood plasma and a method of producing a highly absorbable CoQ10 composition.

16 Claims, No Drawings ns8US 8,491,888 B2

HIGHLY ABSORBABLE COENZYME Q10 COMPOSITION AND METHOD OF PRODUCING SAME

FIELD OF THE INVENTION

The present invention relates to a highly absorbable and bioavailable coenzyme Q10 (CoQ10) composition for nutritional supplementation and for use as an energizer and an antioxidant and in the treatment of many conditions. The present invention is designed to reduce the amount of CoQ10 required to be taken, reduce the expense of CoQ10 supplementation, and provide additional nutritional supplementation. The present invention also relates to a method of increasing the absorption and bioavailability levels of coenzyme Q10 in the blood plasma and a method of producing a highly absorbable CoQ10 composition.

BACKGROUND OF THE INVENTION

CoQ10 is a natural material present in all living cells and organisms. CoQ10 is a key agent responsible for electron transfer in the production of energy in each human cell. CoQ10 is an antioxidant and can be used to treat or improve various conditions and functions within the body. It is especially important for heart health. The normal levels of CoQ10 found in the blood of normal healthy young adults ranges between 0.56 to 1.45 μg/ml (mean=0.81 μg/ml). Some individuals have a low level of natural CoQ10 as a result of diet, genetics, aging, medical conditions or other stresses and they can benefit from CoQ10 supplementation.

Currently CoQ10 for the purpose of supplementation is produced in its pure, crystal form by various manufacturing methods. This form is not well absorbed by the body and therefore requires that high doses be taken in order to be effective. Most common CoQ10 produced for the purpose of supplementation has absorption of about 0.6% to 2.8% of the ingested dose in 6-8 hours and a steady state bioavailability in plasma of 1.4-2.8 μg/mL. Also, it is common to provide about 100 mg of CoQ10 in a 500 mg softgel for the purpose of supplementation. CoQ10 is very expensive and therefore the higher the dose required for supplementation then the more costly. Additionally, oils currently used to dissolve CoQ10 are undesirable solvents and/or inhibit absorption of the CoQ10 by the body.

SUMMARY OF THE INVENTION

One object of the present invention is a CoQ10 composition capable of being highly absorbed by the body for nutritional supplementation and for use as an antioxidant and in the treatment of many conditions.

Another object of the present invention is a CoQ10 composition which is essentially crystal-free.

Another object of the present invention is for a CoQ10 composition which requires less CoQ10 due to a higher absorption level and therefore is less costly to produce.

Still another object of the present invention is for a CoQ10 composition which involves a carrier oil and a solvent which improve CoQ10 absorption.

A further object of the present invention is for a CoQ10 composition which provides increased bioavailability and additional nutritional supplementation.

In accordance with the present invention, an essentially crystal-free CoQ10 composition having the ability to be highly bioavailable and absorbed by the body for nutritional supplementation has been developed. The CoQ10 composition of the present invention includes CoQ10, a solvent, and a carrier oil.

In one embodiment, the CoQ10 composition may also include monoglycerides or diglycerides which aid in the absorption of CoQ10. In another embodiment, the monoglycerides or diglycerides may be from vegetable.

The present invention also relates to a method of increasing the absorption and bioavailability levels of coenzyme Q10 in the blood plasma, wherein the CoQ10 composition of the present invention is administered.

The present invention also relates to a method of producing a CoQ10 composition including mixing the CoQ10, the solvent, and the carrier oil; heating the CoQ10 composition to completely dissolve the CoQ10 into the solvent; and encapsulating the CoQ10 composition in a softgel form for oral delivery and protection of the composition ingredients.

As used herein the term "softgel" is defined as a soft gelatin shell surrounding a liquid for an oral dosage form.

These and other embodiments of the present invention are more fully described in connection with the detailed description.

DETAILED DESCRIPTION OF THE INVENTION

The present invention relates to an essentially crystal-free, highly bioavailable and absorbable CoQ10 composition for nutritional supplementation and for use as an antioxidant and in the treatment of many conditions. The present invention relates to a crystal-free absorbable CoQ10 wherein no CoQ10 crystals are visible by light microscope at magnifications of 640×. The present invention is designed to reduce the amount of CoQ10 required to be taken, reduce the expense of CoQ10 supplementation, and provide additional nutritional supplementation. The present invention also relates to a method of increasing the absorption and bioavailability levels of coenzyme Q10 in the blood plasma and a method of producing a highly absorbable CoQ10 composition.

The CoQ10 composition of the present invention includes CoQ10, a solvent, and a carrier oil. The CoQ10 of the present invention is essentially crystal-free and is highly absorbed into the blood of the human taking the present invention. Suitably, about 7% to 10% of a 100 mg dose of CoQ10 in the present invention is absorbed into the blood in 6 to 8 hours. Further suitably, the level of CoQ10 found in the blood of a human taking daily the CoQ10 composition of the present invention over an extended interval is raised to a steady state above 3 μg/ml.

The CoQ10 composition of the present invention involves less CoQ10 than the prior art due to the higher absorption level of CoQ10. Suitably, the CoQ10 composition of the present invention may be less expensive than the prior art due to the lower amount of CoQ10. In one embodiment, the present invention includes about 50 mg of CoQ10 in about a 700-900 mg softgel. In a further embodiment, the present invention includes about 50 mg of CoQ10 in about an 800-900 mg softgel.

The solvent of the present invention maintains the crystal-free state of the CoQ10 and keeps the CoQ10 in solution. Suitable solvents for use in the present invention can include conjugated linoleic acid (CLA), flax seed oil, ethyl ester marine lipids, citrus oils, or a combination thereof. In accordance with one embodiment, the solvent can include CLA. In another embodiment, the solvent can include citrus oils.

The carrier oil of the present invention aids in improving the absorption level of the CoQ10 into the blood of the human taking the present invention. The carrier oil acts as a transporter for CoQ10 molecules in the passive facillated diffusion process across the absorption cells. Without a lipid carrier the CoQ10 molecules cannot be absorbed. The lipid carrier also increases the volume of an individual dosage of CoQ10 delivered into the intestines of the human taking the present invention, which increases the overall surface area from which the CoQ10 can be absorbed. In one embodiment, the carrier oil of the present invention may be flax seed oil and provides Omega-3 fatty acids and further health benefits. In another embodiment of the present invention, the carrier oil of the present invention may be organic flax seed oil which includes alpha linoleic acid (ALA). In another embodiment of the present invention, the carrier oil may be soy, borage, or marine lipids. Marine lipids are concentrates of ethyl ester EPA/DHA and can be 50% to 90% EPA/DHA combined.

In one embodiment of the present invention, the CoQ10 composition includes capric and caprylic glycerides. Capric and caprylic glycerides are fatty acids which contain monoglycerides and diglycerides and aid in the absorption of the CoQ10 of the present invention. In a further embodiment of the present invention, the CoQ10 composition includes vegetable monoglycerides. The vegetable monoglycerides aid in the absorption of the CoQ10 of the present invention. In another embodiment, a mixture of vegetable monoglycerides and diglycerides may be used.

In one embodiment of the present invention, the CoQ10 composition includes about 50 mg of CoQ10, about 400 mg of conjugated linoleic acid, about 40 mg of capric and caprylic glycerides, and about 200 mg of flaxseed oil.

In another embodiment of the present invention, the CoQ10 composition includes about 50 mg of CoQ10, about 400 mg of conjugated linoleic acid, about 40 mg of vegetable monoglycerides, and about 200 mg of flaxseed oil.

In another embodiment of the present invention, the CoQ10 composition consists of about 50 mg of CoQ10, about 400 mg of conjugated linoleic acid, about 40 mg of vegetable monoglycerides, and about 200 mg of flaxseed oil.

In another embodiment of the present invention, the CoQ10 composition includes about 2-12% by weight CoQ10, about 53-63% by weight conjugated linoleic acid, about 1-11% by weight capric and caprylic glycerides, and about by weight 24-34% flaxseed oil.

In a further embodiment of the present invention, the CoQ10 composition includes about 2-12% by weight CoQ10, about 53-63% by weight conjugated linoleic acid, about 1-20% by weight vegetable monoglycerides, and about 24-34% by weight flaxseed oil.

The CoQ10 composition of the present invention may be orally administered. In another embodiment of the present invention the CoQ10 may be encapsulated into a softgel and orally administered. In a further embodiment of the present invention, the soft gel may be size 14 or 16 oblong. In an alternate embodiment, the present invention may be applied topically. In a further alternate embodiment, the present invention may be a solid or a liquid composition.

The present invention also relates to a method of increasing the absorption and bioavailability levels of coenzyme Q10 in the blood plasma, wherein the CoQ10 composition of the present invention is administered. In one embodiment of the present invention, the absorption level of CoQ10 may be 8-10% of a 100 mg dose of the CoQ10 composition of the present invention in 6-8 hours. In another embodiment of the present invention, the bioavailability level of CoQ10 in the blood plasma may be at least 4 µg/mL.

The present invention also relates to a method of producing a highly absorbable CoQ10 composition. The method includes mixing the CoQ10, the solvent, and the carrier oil; heating the CoQ10 composition to completely dissolve the CoQ10 into the solvent; and encapsulating the CoQ10 composition in a softgel form for oral delivery and protection of the composition ingredients. In one embodiment of the method of the present invention, the CoQ10 is heated to its melting point and vegetable monoglycerides can be added while the temperature is maintained at 35 degrees Celsius. The solvent, followed by the carrier oil are then added. The encapsulation may be completed while maintaining the temperature at 35 degrees Celsius.

EXAMPLE

Peak Absorption and Steady State Bioavailability Testing of the CoQ10 composition of the present invention The peak absorption and steady state bioavailability of the CoQ10 composition of the present invention was tested against traditional crystalline dry powder CoQ10. The study was performed on twenty normal, healthy volunteers. Product A was the CoQ10 composition of the present invention in an encapsulated dosage form and containing about 50 mg of CoQ10, about 400 mg of conjugated linoleic acid, about 40 mg of capric and caprylic glycerides, and about 200 mg of flaxseed oil. Product B was the CoQ10 composition of the present invention in an encapsulated dosage form and containing about 50 mg of CoQ10, about 400 mg of conjugated linoleic acid, about 40 mg of vegetable monoglycerides, and about 200 mg of flaxseed oil. Product C was about 100 mg of the traditional crystalline dry powder CoQ10 in a tablet or hard shell capsule.

A 36-hour peak absorption study was performed. Each volunteer had rested and fasted for at least eight hours prior to beginning the study and control blood samples were taken to test plasma CoQ10 levels. The volunteer was given 100 mg (2 50 mg) oral dosage of either Product A, or Product B along with 240 mL of water and a breakfast meal. A blood sample was taken from each volunteer at 2, 4, 6, 8, 10, 12, 24 and 36 hours to determine the plasma CoQ10 level. During these intervals, no further product was given to the volunteer. The same study was performed with the same volunteers to determine the peak absorption of Product C. The study results are summarized in TABLES 1 and 2, below.

TABLE 1

| | Mean Plasma CoQ10 levels (µg/mL) | | | | | | | | |
|---|---|---|---|---|---|---|---|---|---|
| | 0 hrs | 2 hrs | 4 hrs | 6 hrs | 8 hrs | 10 hrs | 12 hrs | 24 hrs | 36 hrs |
| Product A | 0.93 | 0.94 | 1.34 | 2.23 | 3.02 | 2.00 | 1.50 | 1.33 | 1.24 |
| Product B | 1.05 | 1.10 | 1.79 | 2.63 | 3.07 | 2.17 | 1.73 | 1.43 | 1.47 |
| Product C | 0.90 | 0.94 | 1.01 | 1.14 | 1.12 | 1.03 | 1.01 | 1.06 | 1.02 |

TABLE 2

| | Mean Control Plasma CoQ10 Level (μg/mL) | Mean Plasma CoQ10 Concentration (μg/mL) | Mean AUC$_{(0-12)}$ (μg/mL · hr) | Mean Amount of CoQ10 Absorbed At Cmax (mg) |
|---|---|---|---|---|
| Product A | 0.93 ± 0.20 | 3.02 ± 0.23 | 12.05 ± 2.39 | 8.78 ± 1.93 |
| Product B | 1.05 ± 0.17 | 3.07 ± 0.40 | 13.48 ± 1.48 | 8.49 ± 2.04 |
| Product C | 0.90 ± 0.23 | 1.14 ± 0.23 | 2.6 ± 1.74 | 1.01 ± 0.19 |

Ten volunteers were tested in the 36-hour peak absorption study with Product A. The mean control basal plasma CoQ10 level was 0.93±0.20 μg/mL. The mean $C_{Max}$ occurred in 8 hours and the mean CoQ10 plasma concentration was 3.02±0.23 μg/mL. The mean CoQ10 plasma concentration fell at 12 hours to 1.50±0.26 μg/mL. The mean CoQ10 plasma concentration of 1.24 μg/mL at 36 hours was still significantly greater than the control level of 0.93±0.20 μg/mL. The mean $AUC_{(0-12\ hr)}$ indication of absorption was 12.05±2.39 μg/mL hr. The amount of CoQ10 absorbed at Cmax was 8.78±2.043 mg, which represents 8.78% of the 100 mg dose.

Ten volunteers were tested in the 36-hour peak absorption study with Product B. The mean control basal plasma CoQ10 level was 1.05±0.17 μg/mL. The mean $C_{Max}$ occurred in 6-8 hours and the mean CoQ10 plasma concentration was 3.07±0.40 μg/mL. The mean CoQ10 plasma concentration fell at 12 hours to 1.73±0.34 μg/mL. The mean CoQ10 plasma concentration of 1.47 μg/mL at 36 hours was still significantly greater than the control level of 1.05±0.17 μg/mL. The mean $AUC_{(0-12\ hr)}$ indication of absorption was 13.48±1.48 μg/mL hr. The amount of CoQ10 absorbed at Cmax was 8.49±2.04 mg, which represents 8.49% of the 100 mg dose.

Ten volunteers were tested in the 36-hour peak absorption study with Product C. The mean control basal plasma CoQ10 level was 0.90±0.23 μg/mL. The mean $C_{Max}$ occurred in 6 hours and the mean CoQ10 plasma concentration was 1.14±0.23 μg/mL. The mean CoQ10 plasma concentration fell at 12 hours to 1.01±0.17 μg/mL. The mean CoQ10 plasma concentration of 1.02±0.26 μg/mL at 36 hours was slightly greater than the control level of 0.90±0.23 μg/mL. The mean $AUC_{(0-12\ hr)}$ indication of absorption 2.60±1.74 μg/mL hr. The amount of CoQ10 absorbed at Cmax was 1.01±0.19 mg, which represents 1.01% of the 100 mg dose. The mean total amount absorbed from 0 to 12 hours was 2.6±1.74 μg/mL hr.

The CoQ10 composition of the present invention (Products A and B) had significantly greater plasma CoQ10 levels than the traditional crystalline dry powder CoQ10 (Product C) after the second hour and throughout the remainder of the 36-hour peak absorption study. See Tables 1 and 2.

Each volunteer that participated in the 36-hour peak absorption study also participated in a 28-Day steady state bioavailability study. Each volunteer was given a one month supply of their assigned product, either Product A or Product B. Each volunteer took a single dose each morning with a breakfast containing some fat. The single daily dose was two (2) 50 mg softgel capsules of CoQ10 with breakfast. A test of each volunteer's basal CoQ10 levels was performed on days 7, 14, 21, and 28 after the daily doses were taken. The same study was performed with the same volunteers to determine the steady state bioavailability of Product C. The study results are summarized in TABLES 3 and 4, below.

TABLE 3

| Mean Steady State Bioavailability | Days | | | | |
|---|---|---|---|---|---|
| CoQ10 Level (μg/mL) | 0 | 7 | 14 | 21 | 28 |
| Product A | 0.93 | 2.13 | 2.75 | 3.14 | 3.19 |
| Product B | 1.05 | 2.21 | 2.98 | 3.43 | 3.46 |
| Product C | 0.90 | 1.13 | 1.28 | 1.32 | 1.35 |

TABLE 4

| | Increased Amount Bioavailable at 28 Days (mg) | Mean AUC$_{(0-28)}$ (μg/mL · day) |
|---|---|---|
| Product A | 9.49 ± 2.66 | 43.89 ± 9.10 |
| Product B | 10.12 ± 2.42 | 53.31 ± 8.17 |
| Product C | 1.89 ± 0.78 | 9.85 ± 3.44 |

The plasma CoQ10 increased significantly at 7 days and continued to increase to a plateau after 14 to 21 days for Product A. The 28 day mean steady state bioavailability CoQ10 level was 3.19±0.40 μg/mL and the total amount bioavailable at 28 days was 9.49±2.66 mg. The mean $AUC_{(0-28\ day)}$ index of bioavailability was 43.89±9.10 μg/mL day.

The plasma CoQ10 increased significantly with the steady state bioavailable CoQ10 level occurring in 14 days for Product B. The 21 and 28 day mean steady state bioavailability CoQ10 levels were 3.43±0.53 μg/mL and 3.46±0.49 μg/mL, respectively, and the total amount bioavailable at 28 days was 10.42±2.42 mg. The mean 0 to 28 days AUC index of bioavailability was 53.31±8.17 μg/mL day.

The plasma CoQ10 increased significantly with the steady state bioavailable CoQ10 level occurring in 7 days and remained elevated throughout the 28 day period for Product C. The 21 and 28 day mean steady state bioavailability CoQ10 levels were 1.32 ±0.09 μg/mL and 1.35±0.09 μg/mL, respectively, and the total amount bioavailable at 28 days was 1.89±0.78 mg. The mean total amount absorbed from 0 to 28 days AUC was 9.85±3.44 μg/mL day.

The CoQ10 composition of the present invention (Products A and B) had significantly greater plasma CoQ10 bioavailability levels throughout the 28 day study than the traditional crystalline dry powder CoQ10 (Product C). See Tables 3 and 4. The relative bioavailability of the CoQ10 composition of the present invention was 236% to 256% greater than the traditional crystalline dry powder CoQ10.

Further, it was found that the total percent absorption of the CoQ10 composition of the present invention (Products A and B) was 745% to 783% greater than the traditional crystalline dry powder of CoQ10 (Product C).

While in the foregoing specification this invention has been described in relation to certain preferred embodiments thereof, and many details have been set forth for the purpose of illustration, it will be apparent to those skilled in the art that the invention is susceptible to additional embodiments and that certain details described herein can be varied considerably without departing from the basic principles of the invention.

We claim:

1. A crystal-free coenzyme Q10 composition comprising: non-crystalline coenzyme Q10 present in an amount of 5.3% by weight to about 12% by weight based on the total weight of the composition; a solvent selected from the group consisting of conjugated linoleic acid, ethyl ester marine lipids, citrus oils, and combinations thereof; and a carrier oil.

2. The composition in accordance with claim 1 wherein about 50 mg coenzyme Q10 is encapsulated in a 700-900 mg capacity softgel.

3. The composition in accordance with claim 1 further comprising vegetable monoglycerides.

4. The composition in accordance with claim 3 further comprising vegetable diglycerides.

5. The composition in accordance with claim 1 wherein the solvent comprises conjugated linoleic acid.

6. The composition in accordance with claim 1 wherein the solvent comprises ethyl ester marine lipids.

7. The composition in accordance with claim 1 wherein the solvent comprises citrus oils.

8. The composition in accordance with claim 1 wherein the carrier oil comprises flax seed oil.

9. The composition in accordance with claim 1 wherein the carrier oil is selected from the group consisting of: soy lipids, borage lipids and marine lipids.

10. The composition in accordance with claim 1 wherein the composition is encapsulated in a 14 oblong softgel capsule.

11. A method of increasing coenzyme Q10 levels in blood plasma comprising administering an effective amount of the composition of claim 1 wherein the plasma coenzyme Q10 level is increased significantly from a basal level.

12. The method in accordance with claim 11 wherein the coenzyme Q10 absorption level in the blood plasma is 7-10% of a 100 mg dose of the composition of claim 1 in 6-8 hours.

13. The method in accordance with claim 11 wherein the coenzyme Q10 bioavailability level in the blood plasma is at least 4 µg/mL.

14. A crystal-free coenzyme Q10 composition comprising:
an amount of 5.3% by weight to about 12% by weight non-crystalline coenzyme Q10;
53-63% by weight solvent selected from the group consisting of conjugated linoleic acid, ethyl ester marine lipids, citrus oils, and combinations thereof;
1-20% by weight fatty acids; and
24-34% by weight carrier oil.

15. The crystal-free coenzyme Q10 composition of claim 14 wherein:
the fatty acids are selected from the group consisting of capric and caprylic glycerides, vegetable monoglycerides, vegetable diglycerides and combinations thereof; and
the carrier oil is selected from the group consisting of flax seed oil, soy lipids, borage lipids, marine lipids and combinations thereof.

16. A crystal-free coenzyme Q10 composition comprising:
50 mg non-crystalline coenzyme Q10;
400 mg conjugated linoleic acid;
40 mg vegetable monoglycerides; and
200 mg flax seed oil.

* * * * *